(12) United States Patent
Schaenzer et al.

(10) Patent No.: US 6,185,993 B1
(45) Date of Patent: Feb. 13, 2001

(54) SINGLE SIDED SENSOR FOR GLIDE HEIGHT TESTING

(75) Inventors: Mark J. Schaenzer, Eagan; Zine-Eddine Boutaghou, Vadnais Heights, both of MN (US)

(73) Assignee: Seagate Technology LLC, Scotts Valley, CA (US)

( * ) Notice: Under 35 U.S.C. 154(b), the term of this patent shall be extended for 0 days.

(21) Appl. No.: 09/448,036

(22) Filed: Nov. 23, 1999

Related U.S. Application Data

(62) Division of application No. 08/966,313, filed on Nov. 7, 1997, now Pat. No. 6,023,963.
(60) Provisional application No. 60/044,807, filed on Apr. 24, 1997, and provisional application No. 60/046,314, filed on May 13, 1997.

(51) Int. Cl.[7] ...................................................... G01B 5/28
(52) U.S. Cl. ............................................................. 73/105
(58) Field of Search ................................ 73/105, DIG. 4, 73/862.68; 310/311, 329, 338, 365, 366

(56) References Cited

U.S. PATENT DOCUMENTS

| 4,573,357 | * | 3/1986 | Meunier . | |
|---|---|---|---|---|
| 5,255,016 | * | 10/1993 | Usui et al. . | |
| 5,488,857 | | 2/1996 | Homma et al. | 73/105 |
| 5,640,089 | | 6/1997 | Horikawa et al. | 324/212 |
| 5,672,929 | | 9/1997 | Gutsell et al. | 310/319 |
| 5,689,064 | | 11/1997 | Kennedy et al. | 73/105 |
| 5,773,913 | | 6/1998 | Casselden | 310/338 |
| 5,864,054 | | 1/1999 | Smith, Jr. | 73/105 |

* cited by examiner

*Primary Examiner*—Robert Raevis
(74) *Attorney, Agent, or Firm*—Kinney & Lange, P.A.

(57) ABSTRACT

The present invention is a glide height test slider for detecting asperities and irregularities on a surface of a rotating disc. A slider body has a plurality of edges defining its outer boundaries. The slider body has a piezoelectric element on at least one of its surfaces, and the piezoelectric element does not extend outside the outer boundaries of the slider body. First and second confronting conductors are patterned on the piezoelectric element so that an electric field generated by the piezoelectric element in response to a strain force due to vibration of the slider body induces a voltage between the first and second conductors representative of the vibration. The piezoelectric elements may be a separate element bonded to the slider body, or the slider body may be formed of a piezoelectric material to form the piezoelectric element.

18 Claims, 5 Drawing Sheets

SINGLE SIDED SENSOR FOR GLIDE HEIGHT TESTING

CROSS-REFERENCE TO RELATED APPLICATION(S)

This application is a divisional of U.S. Application Ser. No. 08/966,313, filed Nov. 7, 1997 for "Single Sided Sensor For Glide Height Testing" by M. Schaenzer and Z. Boutaghou, now Pat. No. 6,023,963.

U.S. Application Ser. No. 08/966,313 in turn claims priority from Provisional Application Ser. No. 60/044,807, filed Apr. 24, 1997 for "Method to Energize a Single Sided PZT Crystal for Glide Detection" by M. Schaenzer and Z. Boutaghou, and from Provisional Application Ser. No. 60/046,314 filed May 13, 1997 for "Single Material PZT-Based Slider" by Z. Boutaghou.

BACKGROUND OF THE INVENTION

The present invention relates to a sensor for glide height testing, and more particularly to a test slider assembly including a piezoelectric sensor for detecting asperities on the surface of a disc.

In order to certify that a magnetic disc is adequately smooth for use in a disc drive system, glide height tests must be performed on the disc. Glide height testing is used to verify that a magnetic recording disc is able to accommodate a specified glide height. As the density of data recorded on magnetic discs continues to increase, the flying height of magnetic transducers with respect to the disc must be reduced to accurately read and write information on the disc. As a result, the magnetic recording disc must accommodate the lower glide height of the transducer and the slider supporting it, meaning that the disc surface must be extremely smooth and uniform.

In addition to the general requirement of reduced glide height, magnetoresistive (MR) heads, which utilize an active head element made of a thin layer of NiFe, are extremely sensitive to small physical defects in the surface of the disc, such as undulations on the disc surface and microscopic debris on the disc. When the MR head strikes a defect, there is a momentary frictional heating of the MR element, known as a thermal asperity. This heating effect increases the resistance of the MR head, which causes data errors and loss of information in reading the disc.

A common type of glide height testing is performed by utilizing a test slider having a piezoelectric element bonded thereon. When any part of the slider contacts a protrusion on the surface of the disc, the slider vibrates from the impact. The piezoelectric element bonded to the slider senses the vibration forces acting on the slider, and exhibits a voltage between its terminals representative of the forces experienced by the element. If the vibration force sensed by the piezoelectric element exceeds a predetermined design level, or if vibration occurrences exceed a predetermined design frequency, the disc media under test is not adequately smooth to be used in applications at the glide height being tested.

Previous glide height test sliders mounted the piezoelectric sensor on the slider with a portion of the piezoelectric element extending over the slider edges so that the piezoelectric element could be wired from the top and bottom sides, enabling detection of the voltage across the piezoelectric element by wires connected to each side of the element. However, the extension of the piezoelectric element and the wires connected to the sides of the element created one or more "wings" in the slider or in the piezoelectric element itself, thereby affecting the flying characteristics of the slider and inducing additional vibrational modes. The response of the slider to asperities on the disc media was altered, making it more difficult to accurately deduce the asperity characteristics of the disc from vibrations of the slider. Therefore, there is a need for a glide height test sensor which operates with a test slider without disturbing the original vibrational modes of the slider.

BRIEF SUMMARY OF THE INVENTION

The present invention is a glide height test slider for detecting asperities and irregularities on a surface of a rotating disc. A slider body has a plurality of edges defining its outer boundaries. The slider body has a piezoelectric element on at least one of its surfaces, and the piezoelectric element does not extend outside the outer boundaries of the slider body. First and second confronting conductors are patterned on the piezoelectric element so that an electric field generated by the piezoelectric element in response to a strain force due to vibration of the slider body induces a voltage between the first and second conductors representative of the vibration. The piezoelectric elements may be a separate element bonded to the slider body, or the slider body may be formed of a piezoelectric material to form the piezoelectric element.

One form of the invention is a glide height test slider for detecting asperities and irregularities on a surface of a rotating disc, including a slider body composed of a piezoelectric material. First and second confronting conductors are patterned on the slider body so that an electric field generated by the piezoelectric material of the slider body in response to a strain force on the slider body due to vibration of the slider body induces a voltage between the first and second conductors representative of the vibration.

DETAILED DESCRIPTION OF THE PREFERRED EMBODIMENTS

Figure 1:
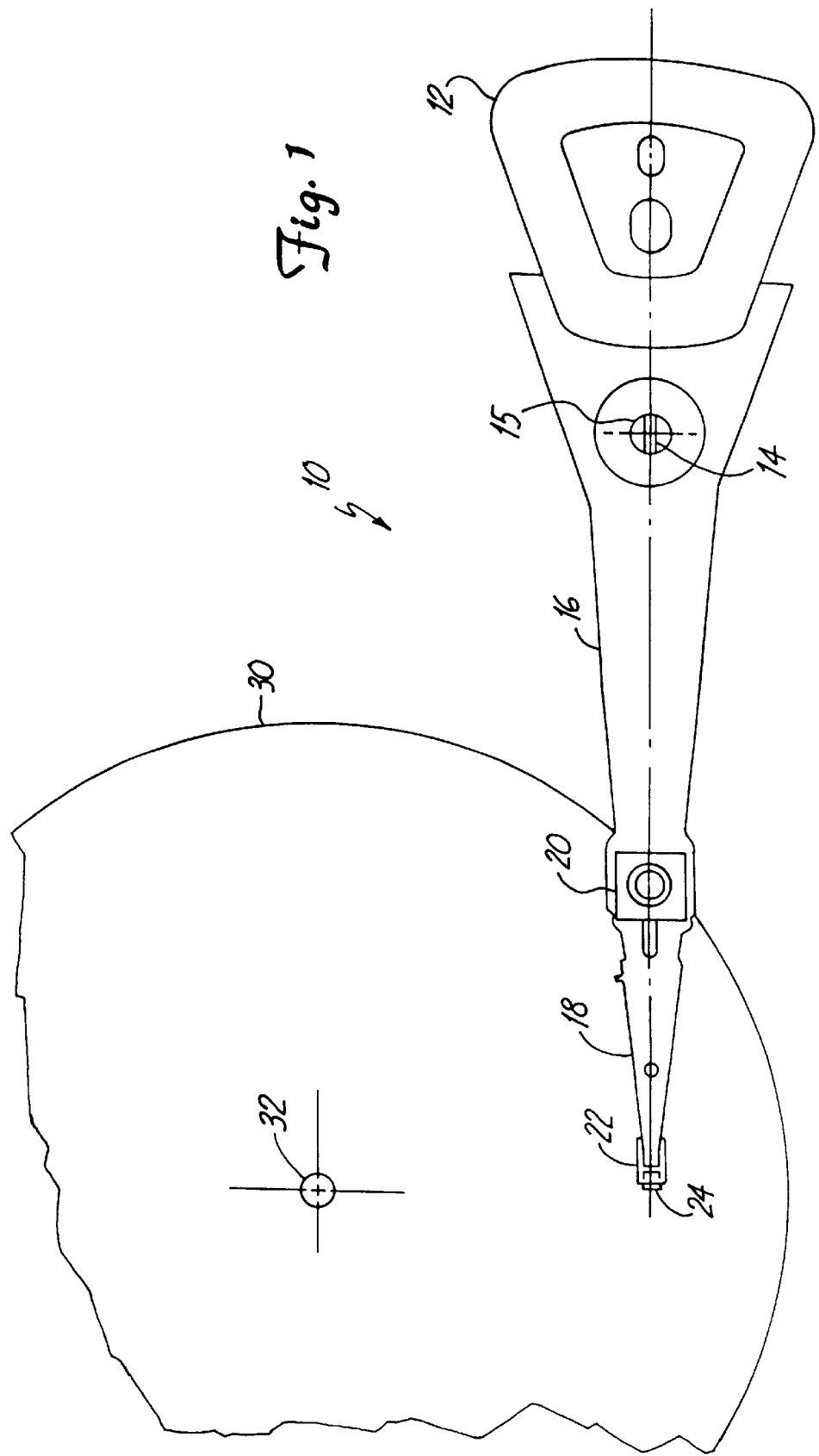
FIG. 1 is a top view of a disc drive system for supporting a slider over the surface of a disc.

FIG. 1 is a top view of a disc test system 10 supporting slider 24 over the surface of disc 30. Test system 10 includes an actuator motor 12 arranged to rotate actuator arm 16 around axis 14 on support spindle 15. Suspension 18 is connected to actuator arm 16 at mounting block 20. Flexure 22 is connected to an end of suspension 18, and carries slider 24. Disc 30 rotates around axis 32 so that windage is encountered by slider 24 to keep it aloft a small distance (the glide height) above the surface of disc 30. Slider 24 includes a piezoelectric element (not shown in FIG. 1) for sensing asperities and irregularities on the surface of disc 30.

Figure 2:
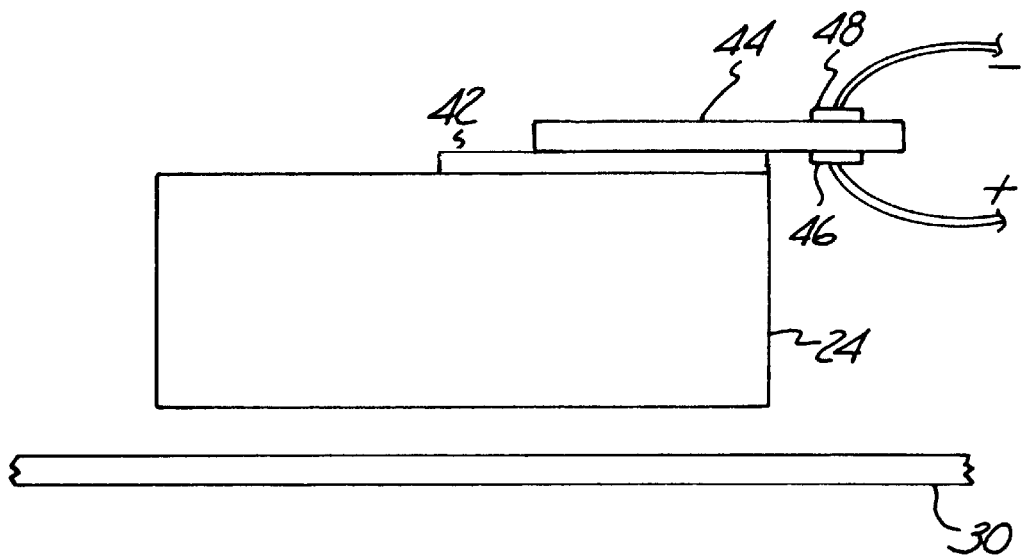
FIG. 2 is a side view of a previous glide height test slider having a piezoelectric element extending over an edge of the slider.

FIG. 2 is a side view of a previous glide height test slider 24 flying over disc 30. Piezoelectric element 44 is attached to slider 24 by bond 42, which, for example, maybe an adhesive material. Piezoelectric element 44 has contacts 46 and 48 on opposite surfaces, so that the voltage difference between the bottom and top surfaces of piezoelectric element 44 can be detected. The vibrational forces acting on slider 24 are determined according to the voltage between contacts 46 and 48.

In use, slider 24 flies over the surface of disc 30, and when any part of slider 24 contacts a protrusion or other irregularity in the surface of disc 30, slider 24 vibrates from the impact. The voltages at contacts 46 and 48 are detected as slider 24 flies over the surface of disc 30, indicating the electric field generated by piezoelectric element 44 in response to the vibration forces acting on the slider. If the magnitude or frequency of occurrence of slider vibrations is too high, the disc media is not sufficiently smooth for use in applications.

The glide height test slider of FIG. 2 is not entirely effective because piezoelectric element 44 extends beyond an edge of slider 24, which is necessary to permit contacts 46 and 48 to be formed on the bottom and top surfaces of the element. As explained above, the extension of piezoelectric element 44 beyond the boundaries of slider 24 has a detrimental effect on the vibrational modes of slider 24, distorting the true vibrational response of slider 24 to an asperity contacted on the surface of disc 30. Because piezoelectric element 44 affects the vibrational response of slider 24, the voltage between contact 46 and 48 does not necessarily truly reflect the forces experienced by slider 24 due to asperities, making the prior glide height test for disc irregularities not altogether reliable.

Figure 3:
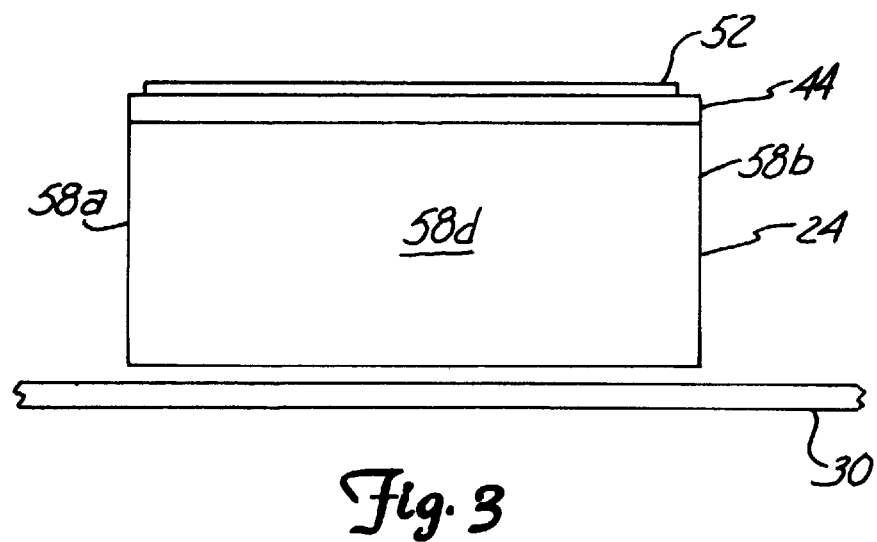
FIG. 3 is a side view of a glide height test slider according to a first embodiment of the present invention.
Figure 4:
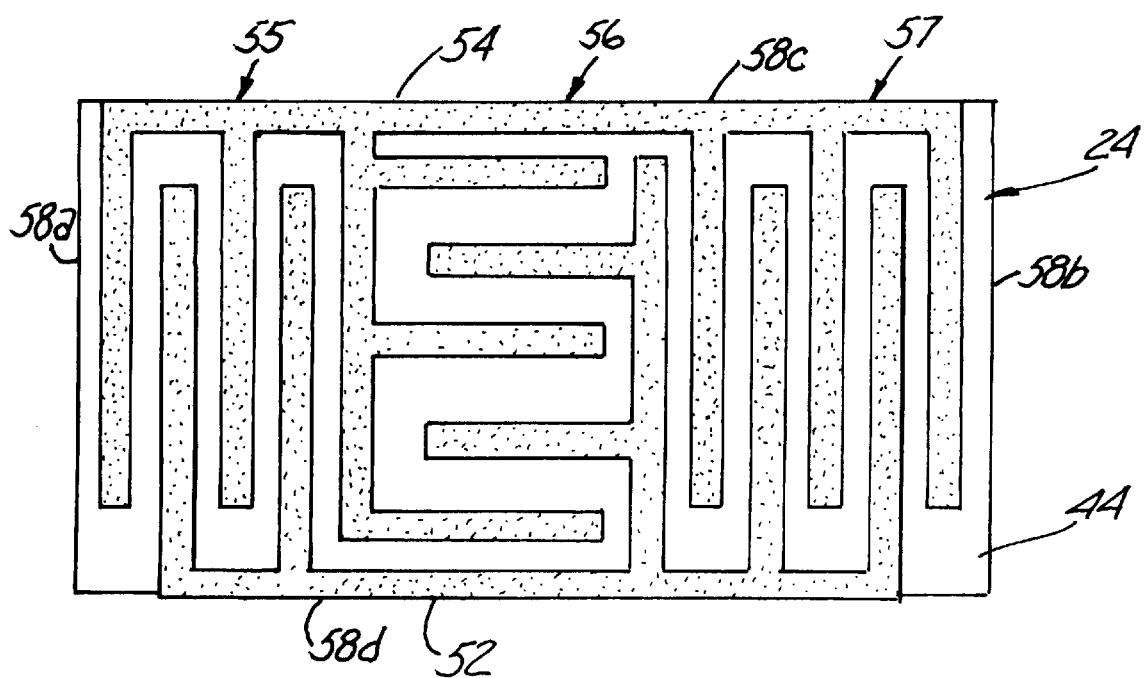
FIG. 4 is a top view of the glide height test slider of FIG. 3.

FIG. 3 is a side view, and FIG. 4 is a top view, of a glide height test slider 24 according to a first embodiment of the present invention. Piezoelectric element 44 is formed on the top surface of slider 24, but does not extend beyond edges 58a, 58b, 58c and 58d forming the outer boundaries of the slider. Conductors 52 and 54 are patterned on a top surface of piezoelectric element 44, creating regions 55 and 57 with parallel lateral legs and region 56 with parallel longitudinal legs. As used herein, "longitudinal" refers to the direction of the longest length of the top surface of slider 24, and "lateral" refers to the direction on the top surface of slider 24 perpendicular to the longest length.

There is a unique relationship between the voltage levels of conductors 52 and 54 and the strain forces experienced by piezoelectric element 44. Therefore, proper interpretation of the voltages of conductors 52 and 54 will reveal the strain characteristic of piezoelectric element 44, from which a determination of the presence, absence and relative size and shape of an asperity on the surface of disc 30 may be made. For example, a compressing strain force in the longitudinal direction and an expanding strain force in the lateral direction in region 56, as might be generated upon impact of slider 24 with a protrusion on the surface of disc 30, would generate a large electric field in the lateral direction, producing a large voltage difference between conductors 52 and 54 in region 56 with parallel longitudinal legs. An expanding strain force in the longitudinal direction and a compressing strain force in the lateral direction in regions 55 and 57 would generate a large electric field in the longitudinal direction, producing a large positive voltage difference between conductors 52 and 54 in regions 55 and 57 with parallel lateral legs. Thus, the voltage difference detected between conductors 52 and 54 may be used to determine the vibrational mode of slider 24 sensed by piezoelectric element 44. Several slider vibration modes are possible, including torsion, longitudinal bending, transverse bending, second torsion, second longitudinal bending, and side bending modes, for example. Each of these modes have distinct bending characteristics at different regions of the slider. The voltage difference between conductors 52 and 54 may be correlated to a particular vibrational mode by empirical calibration or a mathematical model. Therefore, through detection of the vibrational modes of slider 24, asperities on the surface of disc 30 may be readily ascertained.

Figure 5:
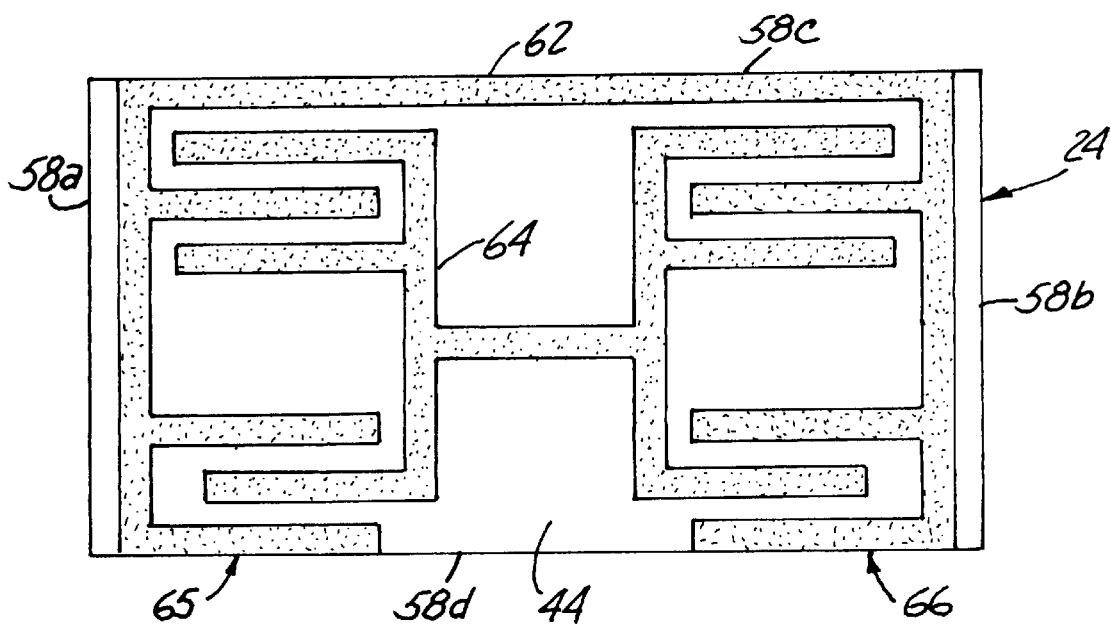
FIG. 5 is a top view of a glide height test slider having patterned conductors according to a second embodiment of the invention.

FIG. 5 is a top view of a glide height test slider 24 according to a second embodiment of the present invention. Piezoelectric element 44 is formed on the top surface of slider 24, but does not extend beyond edges 58a, 58b, 58c and 58d forming the outer boundaries of slider 24. Conductors 62 and 64 are patterned on the top surface of piezoelectric element 44, creating regions 65 and 66 with parallel longitudinal legs, with "longitudinal" again referring to the direction of the longest length of the top surface of slider 24 and "lateral" referring to the direction on the top surface of slider 24 perpendicular to the longest length.

There is a unique relationship between the voltage levels of conductors 62 and 64 and the strain forces experienced by piezoelectric element 44. Therefore, proper interpretation of the voltages of conductors 62 and 64 will reveal the strain characteristic of piezoelectric element 44, from which a determination of the presence, absence and relative size and shape of an asperity on the surface of disc 30 may be made. For example, a compressing strain force in the longitudinal direction and an expanding strain force in the lateral direction, as might be generated upon impact of slider 24 with a protrusion, would generate a large electric field in the lateral direction, producing a large positive voltage difference between conductors 62 and 64 in regions 65 and 66 with parallel longitudinal legs. Thus, the voltage difference detected between conductors 62 and 64 maybe used to determine the vibrational mode of slider 24 sensed by piezoelectric element 44, as discussed above with respect to FIG. 4. Therefore, through detection of the vibrational modes of slider 24, asperities on the surface of disc 30 may be readily ascertained.

Figure 6:
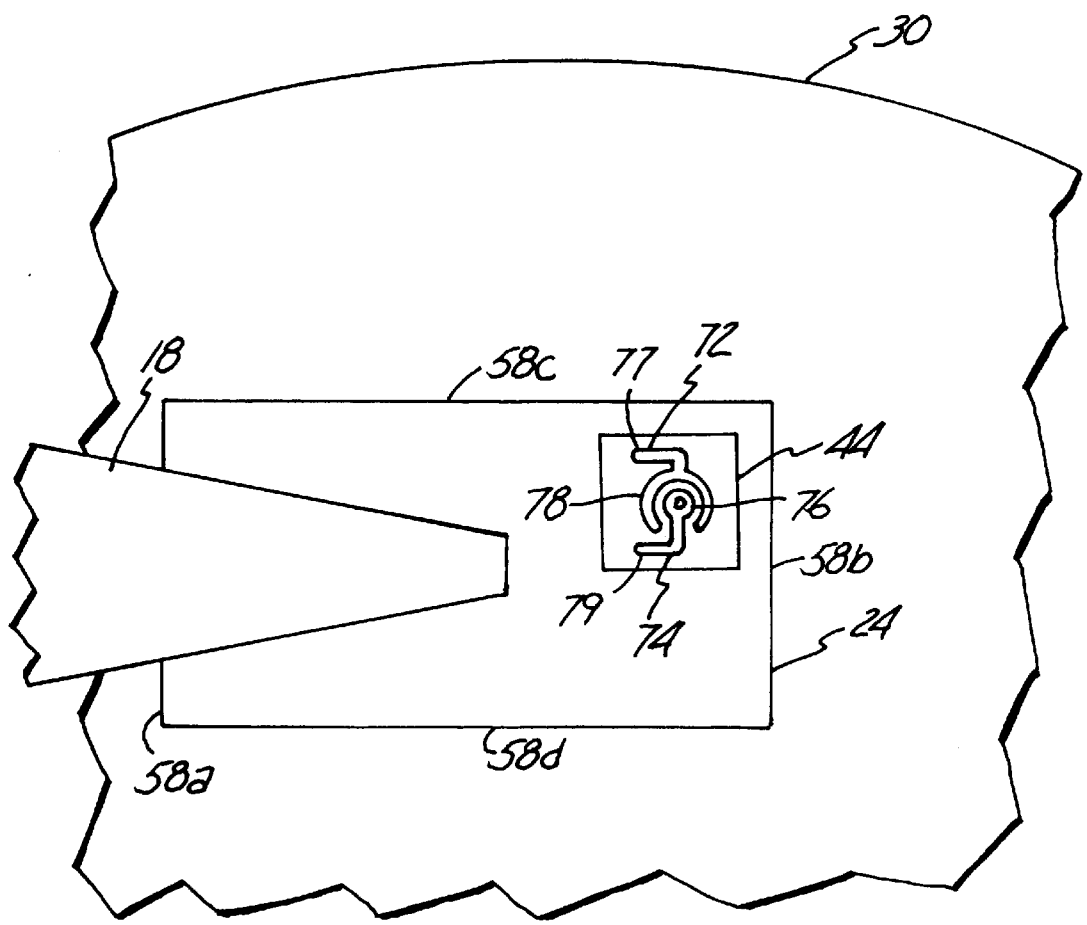
FIG. 6 is a top view of a glide height test slider having patterned conductors according to a third embodiment of the invention.
Figure 7:
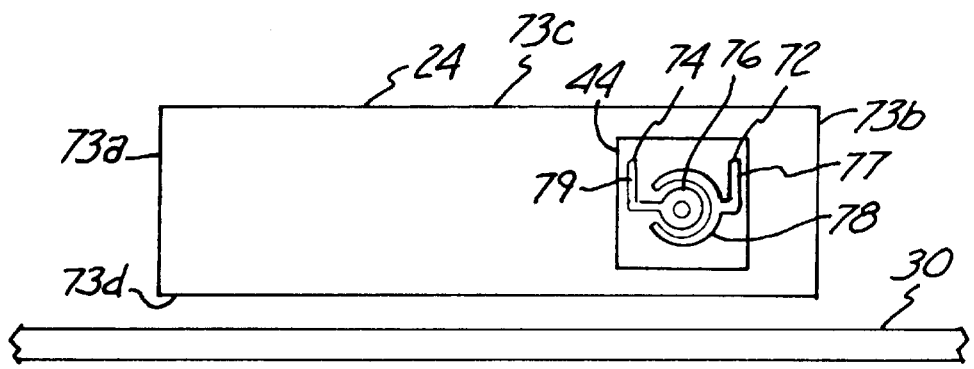
FIG. 7 is an end view of a glide height test slider having patterned conductors according to a fourth embodiment of the invention.

FIG. 6 is a top view of a glide height test slider 24 according to a third embodiment of the present invention, and FIG. 7 is an end view of a glide height test slider 24 according to a fourth embodiment of the present invention.. Piezoelectric element 44 is formed on the top surface of slider 24 in FIG. 6, near the trailing edge of slider 24, and does not extend beyond edges 58a, 58b, 58c and 58d forming the outer boundaries of the slider. In FIG. 7, piezoelectric element 44 is formed on the leading edge or trailing edge surface of slider 24, and does not extend beyond edges 73a, 73b, 73c and 73d forming the outer boundaries of the slider. Load beam 18 applies a pre-load force to slider 24 to maintain its elevation a small distance from disc 30, without contacting piezoelectric element 44 itself. Conductors 72 and 74 are patterned on piezoelectric element 44 in a particular configuration, with conductor 74 forming an inner circle 76 substantially surrounded by an outer circle 78 formed by conductor 72 and with legs 77 and 79 extending from inner circle 76 and outer circle 78, respectively, in a "keyhole" configuration.

There is a unique relationship between the voltage levels of conductors 72 and 74 and the strain forces experienced by piezoelectric element 44. Therefore, proper interpretation of the voltages of conductors 72 and 74 will reveal the strain characteristic of piezoelectric element 44, from which a determination of the presence, absence and relative size and shape of an asperity on the surface of disc 30 may be made, inferred from the vibrational mode of slider 24 detected. The voltage difference between conductors 72 and 74 may be correlated to a particular vibrational mode of slider 24 by empirical calibration or a mathematical model. Therefore, as discussed above with respect to FIGS. 4 and 5, through detection of the vibrational modes of slider 24, asperities on the surface of disc 30 maybe readily ascertained.

Figure 8:
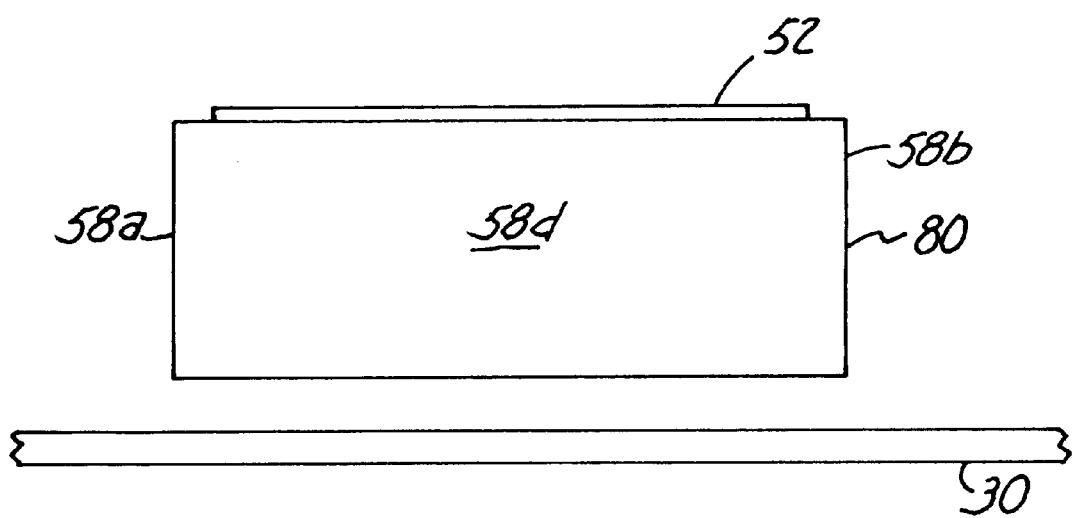
FIG. 8 is a side view of a glide height test slider composed of piezoelectric material according to an alternative embodiment of the present invention.

FIG. 8 is a side view of a glide height test slider 80 composed of piezoelectric material, according to an alternative body of the present invention. Where slider 80 is itself a piezoelectric element, conductors (such as conductor 52) may be patterned as shown in any of FIGS. 4–6 directly on the top surface of slider 80 or as shown in FIG. 7 directly on the leading or trailing edge surface of slider 80, eliminating the need for a separate piezoelectric element to be bonded to the slider. Eliminating the bond simplifies the process of interpreting vibrational modes of the slider from strained forces on the piezoelectric material, since the effect of the bond between the piezoelectric material and the slider no longer needs to be taken into account. Conductors such as 52 may be thin film deposited on the top surface of slider 80 in a configuration such as those shown in FIGS. 4–7.

The present invention provides a glide height test slider configuration to reliably detect asperities on the surface of a rotating disc, without disturbing the vibrational modes of the slider. A single sided piezoelectric sensor having patterned conductors formed thereon is disposed on a surface of the slider, within the slider's outer boundaries. The slider itself may be composed of a piezoelectric material to achieve this result. Vibrational modes of the slider are detected by examining the voltage differences between the patterned conductors on the sensor.

Although the present invention has been described with reference to preferred embodiments, workers skilled in the art will recognize that changes may be made in form and detail without departing from the spirit and scope of the invention. For example, modifications may be made to the patterns and placement of conductors on the glide height test slider; such modifications are within the scope of this invention.

What is claimed is:

1. A glide height test slider for detecting asperities on a surface of a rotating disc, comprising:
   a slider body composed of a piezoelectric material; and
   first and second confronting conductors patterned on the slider body so that an electric field generated by the piezoelectric material of the slider body in response to a strain force on the slider body due to vibration of the slider body induces a voltage between the first and second conductors representative of the vibration.

2. The glide height test slider of claim 1, wherein the first and second conductors are patterned on a top surface of the slider body.

3. The glide height test slider of claim 1, wherein the first and second conductors are patterned on a trailing edge surface of the slider body.

4. The glide height test slider of claim 1, wherein the first and second conductors are patterned on a leading edge surface of the slider body.

5. The glide height test slider of claim 1, wherein the conductors are patterned to form at least one region having parallel longitudinal legs.

6. The glide height test slider of claim 5, wherein the conductors are patterned to further form at least one region having parallel lateral legs.

7. The glide height test slider of claim 1, wherein the conductors are patterned in a keyhole configuration, forming an inner circle substantially surrounded by an outer circle with legs extending from the inner and outer circles.

8. A glide height test slider for detecting asperities on a surface of a rotating disc, comprising:
   a slider body which exhibits a piezoelectric effect in response to strain forces experienced thereby; and
   a plurality of conductors on the slider body so that an electric field generated by the slider body in response to the strain forces on the slider body due to vibration the slider body induces voltage between the conductors representative of the vibration.

9. The glide height test slider of claim 8, wherein the plurality of conductors are on a top surface of the slider body.

10. The glide height test slider of claim 8, wherein the plurality of conductors are on a trailing edge surface of the slider body.

11. The glide height test slider of claim 8, wherein the plurality of conductors are on a leading edge surface of the slider body.

12. A glide height test slider for detecting asperities on a surface of a rotating disc, comprising:
   a piezoelectric slider body; and
   first and second confronting conductors patterned on the piezoelectric slider body to produce voltage therebetween representative of a strain force characteristic of the slider body due to vibrations caused by the slider body contacting an asperity on the surface of the rotating disc.

13. The glide height test slider of claim 12, wherein the first and second conductors are patterned on a top surface of the slider body.

14. The glide height test slider of claim 12, wherein the first and second conductors are patterned on a trailing edge surface of the slider body.

15. The glide height test slider of claim 12, wherein the first and second conductors are patterned on a leading edge surface of the slider body.

16. The glide height test slider of claim 12, wherein the first and second conductors are patterned to form at least one region having parallel longitudinal legs.

17. The glide height test slider of claim 12, wherein the first and second conductors are patterned to further form at least one region having parallel lateral legs.

18. The glide height test slider of claim 12, wherein the first and second conductors are patterned in a keyhole configuration, forming an inner circle substantially surrounded by an outer circle with legs extending from the inner and outer circles.

* * * * *

UNITED STATES PATENT AND TRADEMARK OFFICE
CERTIFICATE OF CORRECTION

PATENT NO. : 6,185,993 B1
DATED : February 13, 2001
INVENTOR(S) : Mark J. Schaenzer It is certified that error appears in the above-identified patent and that said Letters Patent is hereby corrected as shown below:

<u>Column 6,</u>
Line 20, after "vibration", insert -- of --

Signed and Sealed this

First Day of January, 2002

Attest:

JAMES E. ROGAN
*Attesting Officer*  *Director of the United States Patent and Trademark Office*